(12) United States Patent
Brooks et al.

(10) Patent No.: US 7,806,879 B2
(45) Date of Patent: Oct. 5, 2010

(54) MEDICAL SUCTION SYSTEM

(75) Inventors: Christine N. Brooks, Alcoa, TN (US);
Walter C. Cowart, Blaine, TN (US);
Terry B. Kehne, Knoxville, TN (US);
Timothy R. Rowen, Corryton, TN (US);
Eric A. Ward, Knoxville, TN (US); E.
Steven Ward, Knoxville, TN (US)

(73) Assignee: DeRoyal Industries, Inc., Powell, TN (US)

(*) Notice: Subject to any disclaimer, the term of this patent is extended or adjusted under 35 U.S.C. 154(b) by 5 days.

(21) Appl. No.: 12/057,999

(22) Filed: Mar. 28, 2008

(65) Prior Publication Data
US 2009/0247968 A1    Oct. 1, 2009

(51) Int. Cl.
*A61M 1/00* (2006.01)

(52) U.S. Cl. .................. 604/319; 604/317; 604/318; 604/320; 604/321; 604/322; 604/323

(58) Field of Classification Search .................. 604/319, 604/320, 322, 317, 318, 321, 323
See application file for complete search history.

(56) References Cited

U.S. PATENT DOCUMENTS

| | | | |
|---|---|---|---|
| 3,240,501 A * | 3/1966 | Smith | 277/614 |
| 3,590,440 A * | 7/1971 | Cook, Jr. | 425/153 |
| 3,814,098 A | 6/1974 | Deaton | |
| 3,915,189 A * | 10/1975 | Holbrook et al. | 137/205 |
| 4,013,076 A * | 3/1977 | Puderbaugh et al. | 604/320 |
| 4,111,204 A | 9/1978 | Hessel | |
| 4,112,947 A * | 9/1978 | Nehring | 604/30 |
| 4,321,922 A | 3/1982 | Deaton | |
| 4,379,455 A * | 4/1983 | Deaton | 604/320 |
| 4,419,093 A | 12/1983 | Deaton | |
| 4,430,084 A | 2/1984 | Deaton | |
| 4,449,984 A * | 5/1984 | Cruz | 604/319 |
| 4,681,571 A * | 7/1987 | Nehring | 604/320 |
| 5,306,257 A * | 4/1994 | Zdeb | 604/131 |
| 5,637,104 A * | 6/1997 | Ball et al. | 604/319 |
| 5,669,892 A | 9/1997 | Keogh et al. | |
| 5,975,096 A | 11/1999 | Dunn et al. | |

* cited by examiner

*Primary Examiner*—Tatyana Zalukaeva
*Assistant Examiner*—Ginger T Chapman
(74) *Attorney, Agent, or Firm*—Luedeka, Neely & Graham, PC (57) ABSTRACT

A disposable liner/lid system useable with a rigid canister and having an adhesive seal to provide improved sealing characteristics and effectively reduce the likelihood of spillage and leakage. The liner includes a flange and the lid includes adhesive that is secured to the interior of the lid and the flange of the liner when installed to provide a seal.

10 Claims, 8 Drawing Sheets

FIG. 8

MEDICAL SUCTION SYSTEM

FIELD

This disclosure relates to the field of medical suction devices. More particularly, this disclosure relates to a medical suction system that utilizes a rigid canister in conjunction with a semi-rigid disposable liner and has improved construction for sealing against spillage.

BACKGROUND

Conventional medical suction systems of the type having a rigid canister and a conventional semi-rigid disposable liner within the canister have many disadvantages. The semi-rigid liners can easily rupture and the structure and manner of installation of the lids of the systems leaves such systems vulnerable to leakage or spillage. Accordingly, improvement is desired.

SUMMARY

The above and other needs are met by a medical suction system which includes a canister, a liner received within the canister, and a lid installed on the canister and liner.

The lid includes a peripheral seal member extending from an interior surface of the lid and positionable to bear against a portion of the rigid canister to provide a seal between the atmosphere and exterior portions of the liner located within the canister. A peripheral adhesive material is adhered to the interior surface of the lid adjacent the peripheral seal member and positionable to adhere to the flange of the liner when the lid is installed on the liner to provide a seal between the interior of the liner and locations exterior the liner.

The liner and the lid are disposable. When the liner is full of suction fluids, the liner is removable from the canister with the lid remaining installed on the liner by the adhesive. The liner and the lid provide improved sealing characteristics and effectively reduce the likelihood of spillage and leakage as compared to conventional liner/lid systems.

BRIEF DESCRIPTION OF THE DRAWINGS

Further advantages of the disclosure are apparent by reference to the detailed description when considered in conjunction with the figures, which are not to scale so as to more clearly show the details, wherein like reference numbers indicate like elements throughout the several views, and wherein.

DETAILED DESCRIPTION

With initial reference to FIGS. 1-6, the disclosure relates to a medical suction system 10 having a rigid canister 12, a semi-rigid liner 14, and a lid 16. A mount 18 is provided at the use location for positioning of the system 10 onto a wall or other support surface, and for placing the system 10 in flow communication with a source of negative pressure V, such as a hospital suction line.

The canister 12 is configured to remain positioned on the mount 18 as a substantially permanent fixture at the location, such as a hospital room. The liner 14 and lid 16 are single-use disposable components of the system 10. Thus, when the liner 14 is substantially full of suction fluids, the liner 14 with the lid 16 are removed from the canister 12 for disposal. The liner 14 and lid 16 are advantageously configured to provide improved sealing characteristics and effectively reduce the likelihood of spillage and leakage as compared to conventional liner/lid systems.

The rigid canister 12 is made of a substantially rigid material, preferably a clear and transparent plastic material such as polycarbonate. A preferred material is a polycarbonate resin available under the designation Calibre 201-15 from Dow Chemical Company. The canister 12 is sufficiently rigid so as to unbreakable and uncollapsible during normal use. The canister 12 is essentially cup-shaped with a bottom 20 and a surrounding sidewall 22 extending from the bottom to an open upper end 24. However, to provide the desired anti-spillage and anti-leakage characteristics to the system 10, the canister 12 is configured so that the upper end 24 is of a desired shape compatible with both the liner 14 and the lid 16. A vacuum port 26 extends through the sidewall 22 for connection to the mount 18 so that the interior of the canister 12 (and the exterior of the liner 14 when installed therein) is in flow communication with the source of negative pressure. Thus, it will be understood that substantially equal pressure is applied to both the interior and exterior of the liner 14 during use of the system 10.

Figure 6:
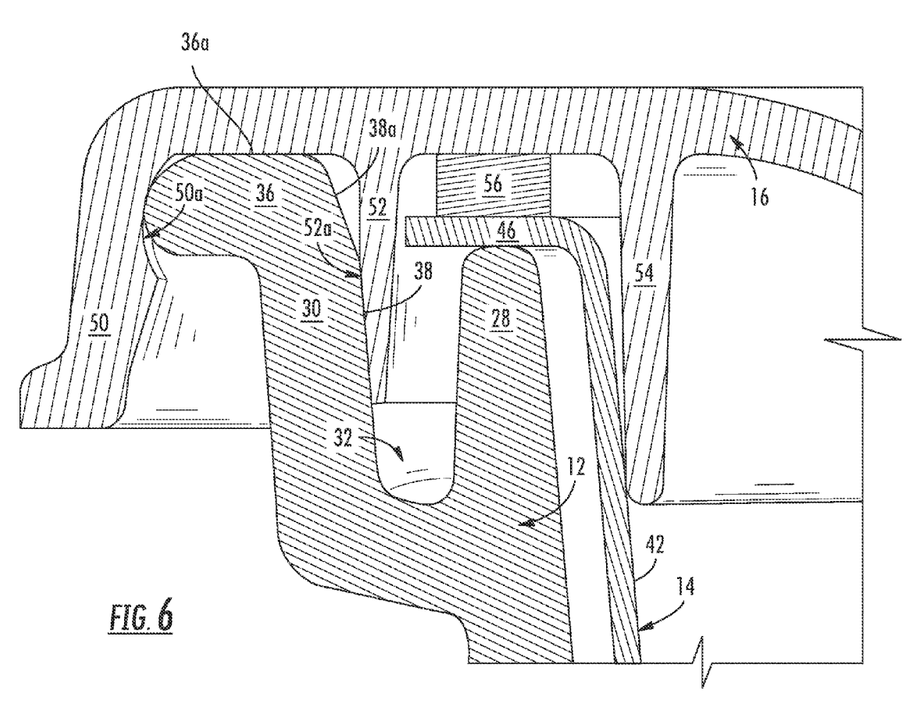
FIG. 6 is a detailed partial cross-sectional side view showing the lid installed.

With particular reference to FIG. 6, the upper end 24 of the canister 12 includes a first peripheral upstanding member 28 defined by an upper end of the sidewall 22, and a second peripheral upstanding member 30 extending from an exterior portion of the sidewall 22 radially outward of the first member 28 and configured to extend to a height above the height of the member 28 and to define a peripheral blind bore 32 between the first upstanding member 28 and the second upstanding member 30. As explained below, the height of the member 28 (and hence the depth of the bore 32) is selected to exceed that of the potential distance the liner 14 may expand during use. The term "peripheral" is used herein to describe surrounding characteristics. However, it will be understood that while the canister, liner, and lid shown have circular cross-sections, other cross-sectional shapes may be utilized, e.g., oval, triangular, square, with the peripheral characteristics represented by correspondingly shaped non-circular encircling or peripheral structures.

The first upstanding member 28 is preferably formed as a standing rib to support a portion of the liner 24, as described more fully below. To facilitate a snap-fit relationship between the canister 12 and the lid 16, the second upstanding member 30 includes a terminal end shaped to have a flange 36 having an upper flat surface 36a and configured to snap-fit with the lid 16. In addition, the upstanding member 30 also includes an inner chamfered edge 38 adjacent the bore 32 to engage a portion of the lid 16 to provide a seal between the exterior of the liner 14 and the atmosphere, described in more detail below. An upper portion 38a of the edge 38 is preferably oriented at a shallower pitch to provide a guide for facilitating seating of the lid 16.

The liner 14 may be of conventional molded plastic construction and sized to be fit within and conform to the canister 12. The liner 14 includes a bottom 40 and a surrounding sidewall 42 extending from the bottom to an open upper end 44 which defines an outwardly extending peripheral flange 46 oriented to be substantially flat and planar and extending horizontally (relative to the generally vertical length axis of the liner 14) from the upper end 24.

In a preferred embodiment, it is preferred that the liner 14 be injection molded as opposed to being thermoformed. It has been observed that injection molded liners offer improved wall strength and resist splitting as is common to conventional thermoformed liners. The liner 14 is also preferably semi-rigid so as to be of a lower cost than a rigid liner. That is, the liner 14 is substantially self-supporting, unlike a plastic bag that cannot stand on its own, but is relatively thin and flexible in the manner of a disposable plastic drinking cup. In this regard, preferred materials for making semi-rigid liners using injection molding techniques are resinous polymers such as co-polymer polypropylene resins available from Flint Hills Resources, LP of Wichita, Kans., with a particularly preferred resin being available from Flint Hills Resources under the designation P9-053X. Another advantage associated with the use of injection molding techniques is that such techniques enable stack tabs 48 to be provided on the bottom 40 of the liner 14. Stack tabs are advantageous to provide an air path to avoid pressure adhesion of stacked liners and facilitate separation of stacked liners 14.

Figure 7:
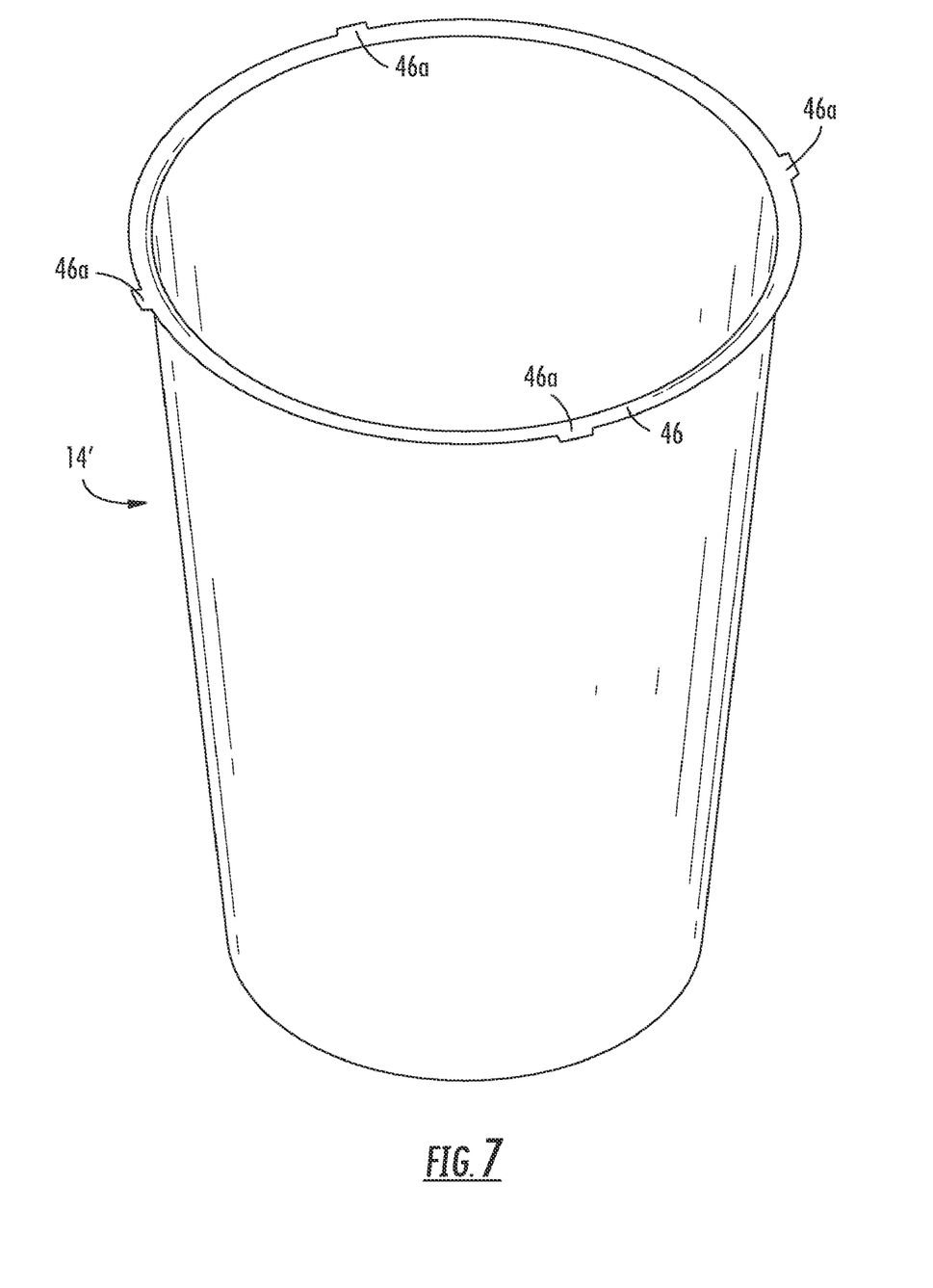
FIG. 7 shows an alternative embodiment of a liner for use with the system of FIG. 1 that includes a plurality of alignment tabs.

With reference to FIG. 7, there is shown an alternate embodiment of a liner 14' that is substantially identical to the liner 14, except that flange 46' thereof includes a plurality of alignment tabs 46a extending outwardly therefrom.

Figure 1:
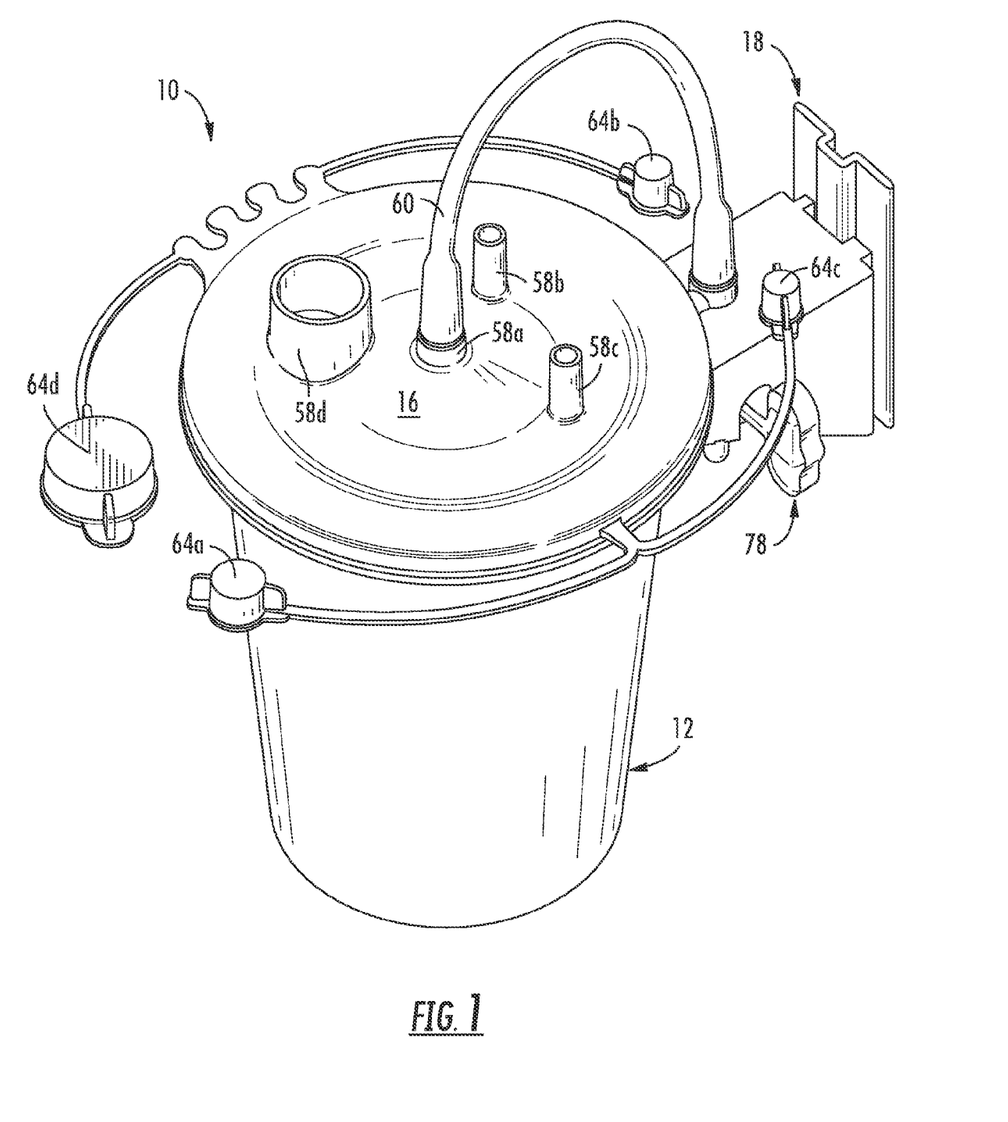
FIG. 1 is a perspective view of a suction system according to the disclosure.
Figure 2:
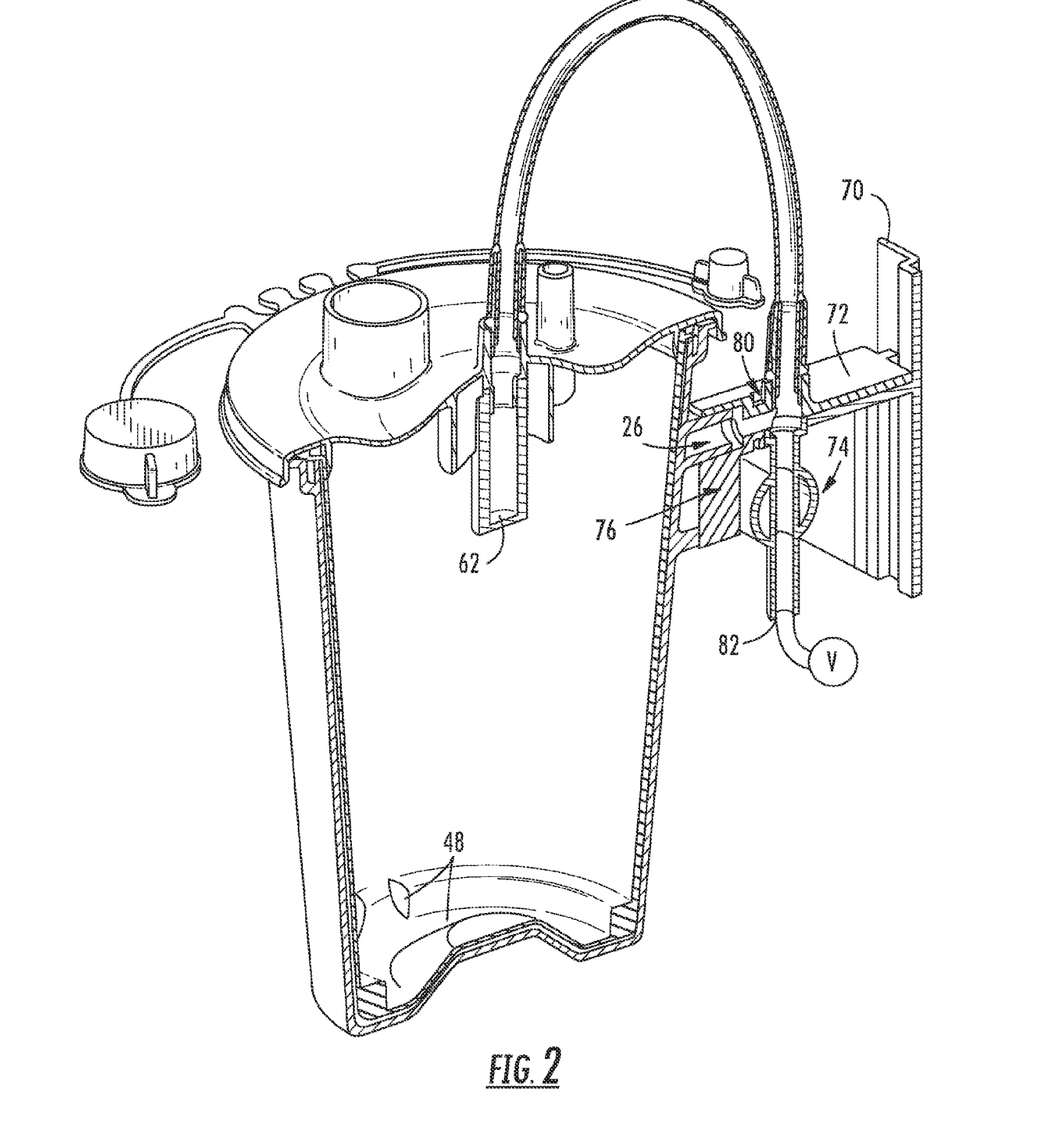
FIG. 2 is a cross-sectional perspective view of the system of FIG. 1.
Figure 3:
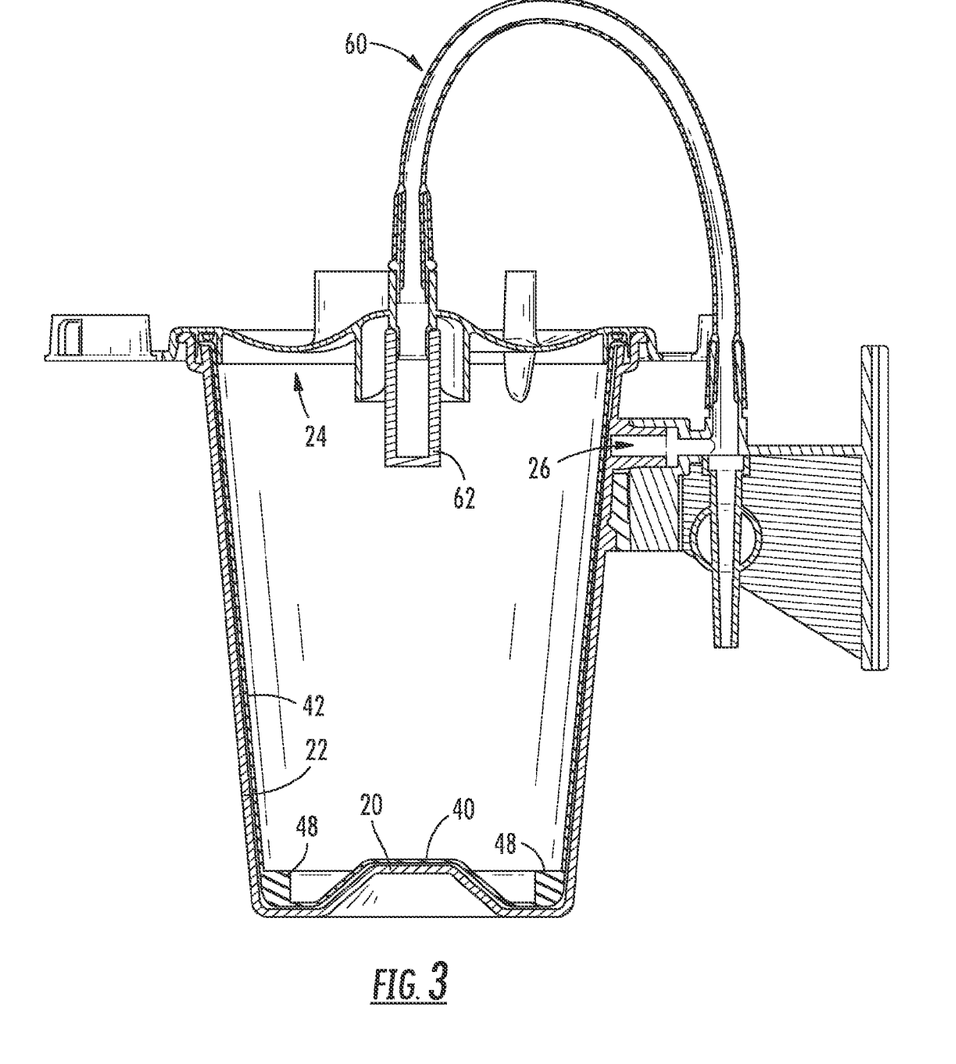
FIG. 3 is a cross-sectional side view of the system of FIG. 1.
Figure 4:
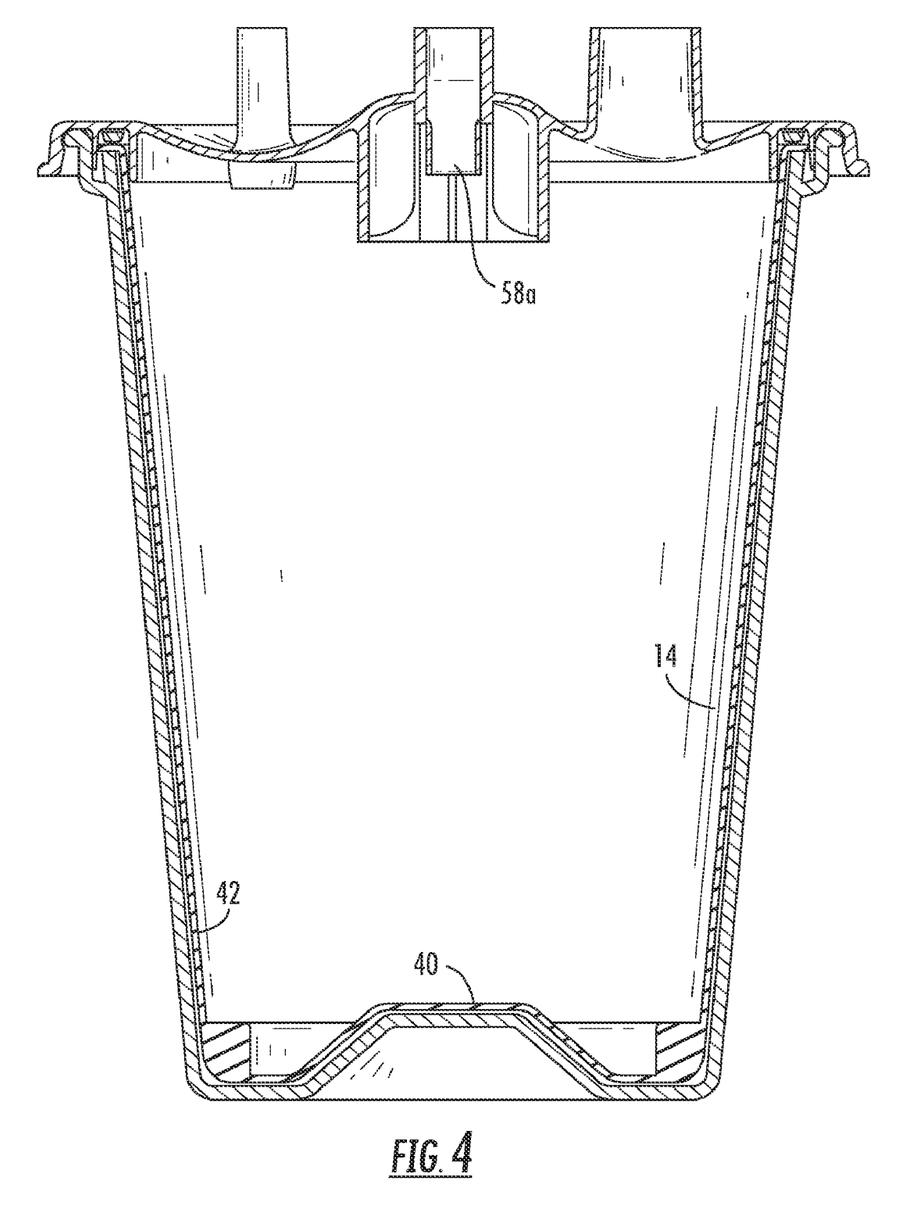
FIG. 4 shows the view of FIG. 3 with some of the components removed.
Figure 5:
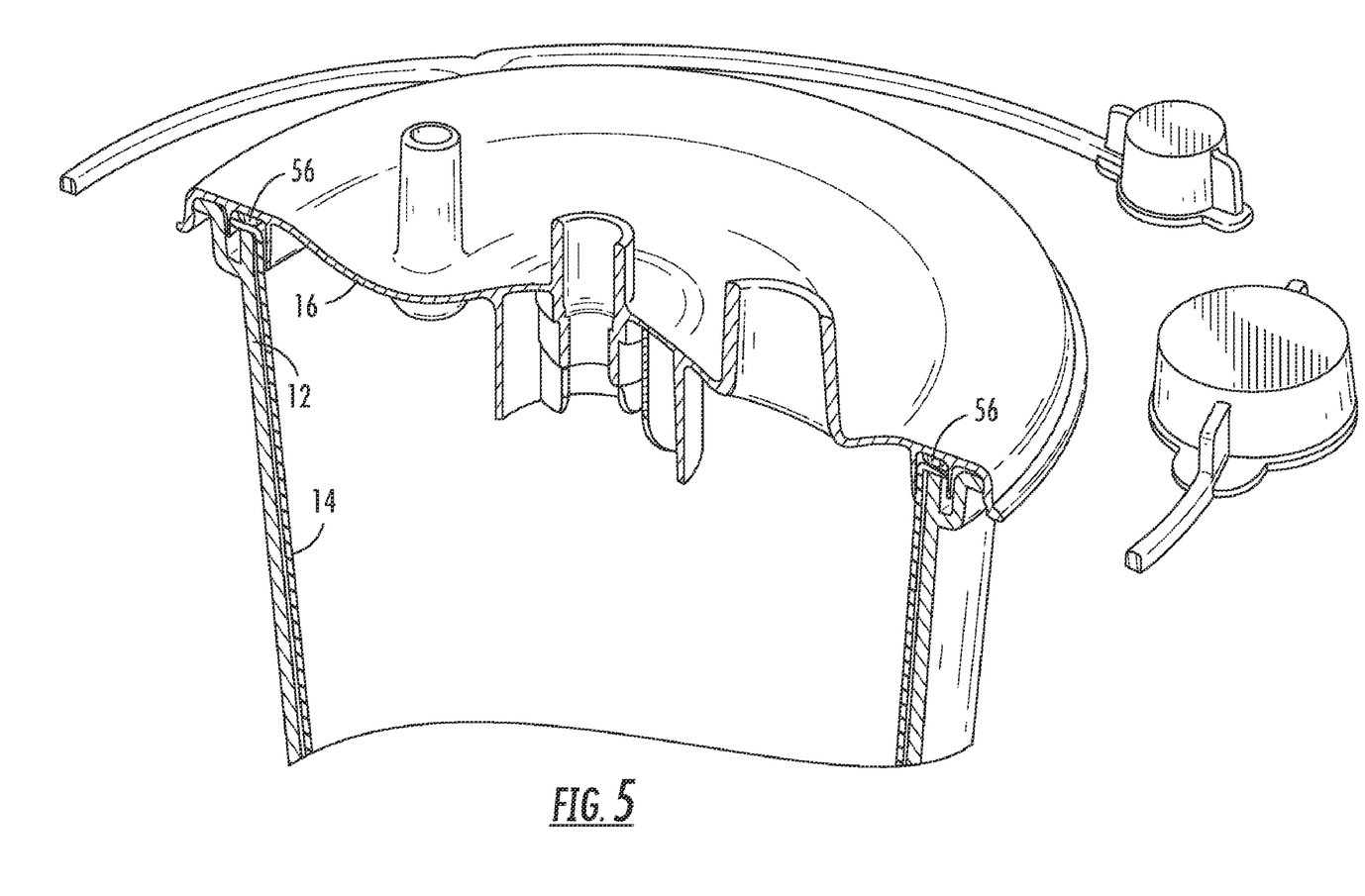
FIG. 5 is a partial cross-sectional perspective view of the system of FIG. 1, showing a lid installed.

The lid 16 is preferably of one-piece molded plastic construction and includes a peripheral snap ring 50 defining the outer periphery, a peripheral seal ring 52 extending from the interior surface of the lid 16 and spaced apart from and radially interior the snap ring 50 and a peripheral pilot ring 54 interior the seal ring 52. An adhesive material 56 is provided as a peripheral ring between the seal ring 52 and the pilot ring 54. Some or all of various ports 58a-58d or additional ports may be defined through the lid 16 interior of the pilot ring 54 so as to be in flow communication with the liner 14 of the assembled system 10.

With reference to FIG. 6, an inner surface 50a of the snap ring 50 is preferably shaped to matingly engage the shape of the flange 36. For example, as shown, the inner surface 50a is generally concave, while the flange 36 is generally convex so as to fittingly engage one another when the lid 16 is installed. As will be appreciated, other mating profiles may be utilized.

The inner seal ring 52 is tapered so as to provide an outer tapered surface 52a configured to fittingly engage the inner chamfered edge 38 of the upstanding member 30 of the canister 12 and provide a seal along the interface of the edge 38a and the surface 52a, so as to seal between the atmosphere and the outside of the liner 14.

The pilot ring 54 is configured to extend just interior the sidewall 42 of the liner 14 and is of greater length than the rings 50 and 52 so that the lid 16 is self-aligning with the liner 14 and the canister 12 in which the liner is installed.

Preferred adhesive materials 56 are pressure sensitive adhesives. A preferred pressure sensitive hot melt adhesive is available from Henkel Corporation under the designation "Euromelt 808697." The Euromelt product is preferably applied to have a width of about 0.2 inches and a thickness of about 0.1 inches, with an edge of the adhesive material 56 abutting the pilot ring 54, with some gap left adjacent the seal ring 52 to allow for spreading of the adhesive when the lid 16 is installed, since the application of pressure (manual and via suction applied to the system 10) will compress the thickness of the adhesive and increase its width. That is, when the lid 16 is installed, the adhesive 56 is adhered to both the inner surface of the lid and the flange 46 of the liner 14 to provide a seal that is effective as a seal between the interior of the liner 14 and locations exterior the liner 14. As will be appreciated, the seal is effective to prevent fluids, including pressurized air, from passage. In this regard, and with reference to FIG. 6, it will be appreciated that the upper flat surface 36a of the flange is spaced a distance above the member 28 substantially corresponding to the thickness of the flange 46 of the liner 14 and the thickness of the adhesive 56, such that the flange 36 is snap-fit to the lid 16 and the adhesive 56 is slightly compressed.

Port 58a is a vacuum port that connects via a line 60 to the mount 18 for placement in flow communication with a source of negative pressure. A shutoff mechanism is provided by a filter 62 located in flow communication with the port 58a on the interior side of the lid 16 to prevent any reverse flow of contents collected in the liner 14 through the port 58a. That is, while the filter 62 does provide air filtration, it has a primary function of preventing non-gaseous contents of the liner from being sucked into the vacuum line. The filter 62 is preferably a solid provided by a blend of polyethylene powder and carboxymethylcellulose powder (CMC) sintered into the desired shape using heat and pressure, such as described in U.S. Pat. No. 6,780,309, incorporated herein by reference in its entirety. As liquids are drawn into the filter 62, such as when the liner 14 becomes full, the CMC increases the viscosity of the liquid to the point where it will no longer pass through the pores of the filter, thus shutting off flow communication between the vacuum source and the interior of the liner and preventing liquid from passing through the filter 62. However, it will be understood that other shutoff mechanisms may be used, such as a mechanical float shutoff mechanism.

Ports 58b and 58c are connectable to a line running from the patient for travel of substances to be collected from the patient. Port 58d is a pouring port for emptying of the liner 14 if desired. Caps 64a-64d are provided for the ports 58a-58d, respectively.

The mount 18 is of molded plastic construction and includes a base 70, a body 72 extending from the base 70 and housing a valve 74, and a receiver 76. The base 70 is securable to a wall or other support surface. The valve 74 functions as an on/off switch for application of vacuum to the system and also enables adjustment of the air volume passing through the system 10. The valve 74 may be provided as by a rotary valve having a rotatable handle 78 that may be turned to selectively block a passage for adjusting flow through the valve 74. An entrance end of the valve 74 is placeable in flow communication with the source of negative pressure V. An opposite port end of the valve 74 is configured to have outlets 80 and 82. The outlet 80 is placeable in flow communication with the line 60. The receiver 76 is configured for mountably receiving the canister 12 and for placing the vacuum port 26 of the canister in flow communication with the outlet 80 of the valve 74. The outlet 82 is placeable in flow communication with the source of negative pressure V, typically being connected to an external vacuum regulator upstream of the system 10 as a component of the source of negative pressure V.

To assemble the system 10, mount 18 is secured to a wall or other support by the base 70 using fasteners or the like. The canister 12 is received by the receiver 76 such that the port 26 of the canister 12 is connected to the port 82. At this point, the handle 78 is positioned so that the valve is cutoff from the source V. The liner 14 is then joined to the lid 16 as by locating the pilot ring 54 of the lid 16 within the liner 14 and pressing the liner 14 and the lid 16 together so as apply pressure to the interface of the flange 46 of the liner 14 and the adhesive 56. In this regard, when using the liner 14', it has been observed that the tabs 46a further assist in ensuring that the liner 14' and the lid 16 are concentric. Returning to FIG. 6, it will be seen that the flange 46 does not extend to touch the adjacent surface of the ring 52. In this regard, the tabs 46a are preferably sized to extend to the ring 52. The tabs 46a also advantageously provide room for any excess of the adhesive 56 to escape outwardly of the liner 14. If the liner 14' is used, it will be understood that the pilot ring 54 may be omitted from the lid 16. However, it is preferred that the lid 16 having the pilot ring 54 be utilized with the liner 14' due to the advantages of the ring 54 in inhibiting inward creep of the adhesive 56.

The thus assembled liner 14 having the lid 16 is positioned within the canister 12 such that the seal ring 52 of the lid 16 is within the peripheral bore 32 and the inner chamfered edge 38 of the lid is in contact with the outer tapered surface 52a of the seal ring 52. Next, the snap ring 50 is pressed over the flange 36 until a snap-fit is achieved. The line 60 is attached to the port 58a, the port 58b is attached to a patient line, the port 58c is either capped with cap 64c or attached to a patient line, and the cap 64d is installed on the port 58d. Finally, the handle 78 is desirably rotated so that a desired negative pressure is supplied via the valve 74.

In this regard, during use of the system 10, it will be understood that negative pressure is applied to both the interior and exterior of the liner 14. Negative pressure supplied to the interior of the liner 14 pulls substances to be collected through the port 58b (and optionally 58c). Negative pressure supplied via the port 26 to the exterior of the liner 14 within the canister 12 maintains the liner 14 from collapsing. As the liner 14 becomes full of collected substances, the weight of the contents tends to expand the liner 14 and force the bottom 40 of the liner 14 against the bottom 20 of the canister 12 and the sidewall 42 of the liner 14 expands against the sidewall 22 of the canister 12. Finally, once the liner 14 is full, the liquids therein come into contact with the filter 62 which responds by swelling and decreasing the application of negative pressure into the liner and soon ceasing the application of negative pressure into the liner. At this point, the pressure applied to the exterior of the liner 14 is greater than the interior pressure, further expanding the liner 14. As this expansion occurs, the forces resulting from the expansion also act on the flange 46. However, the upstanding member 28 serves to support the flange 46. Thus, the height of the member 28 is selected to be greater than the potential elongate expansion of the liner 14 to maintain the flange 46 on the member 28. In this regard, it will be further understood that the adhesive 56 and the lid 16 also serve to maintain the flange 46 seated on the member 28.

At the point that the liner 14 is full, it is desirable to rotate the handle 78 to turn of the valve 74, with the remaining caps being placed over the respective uncovered ports. As pressure equalization occurs, a slight relaxation of the liner 14 is typical, in that the liner 14 unexpands slightly from the removal of the application of negative pressure to its exterior. In the case of conventional liner/lid systems, leakage is very common at this point. However, it has been observed that the system according to the disclosure achieves improved results and substantially avoids leakage or spillage. Likewise, if a conventional filled liner/lid is knocked over, spillage will occur. Advantageously, the system according to the disclosure has been observed to not leak or spill or to substantially reduce leakage or spillage when knocked over.

The system 10 is also advantageously configured to reduce space for storage and shipping. For example, liners 14 and 14' are readily stackable and the lids 16 are relatively flat and amendable to storage in a bag. The liners 14 and 14' and lids 16 are also easy and convenient to use. For example, the liners 16 may readily be unstacked and the alignment features of the lids facilitate quick and secure connection of the lids to the liners.

Figure 8:
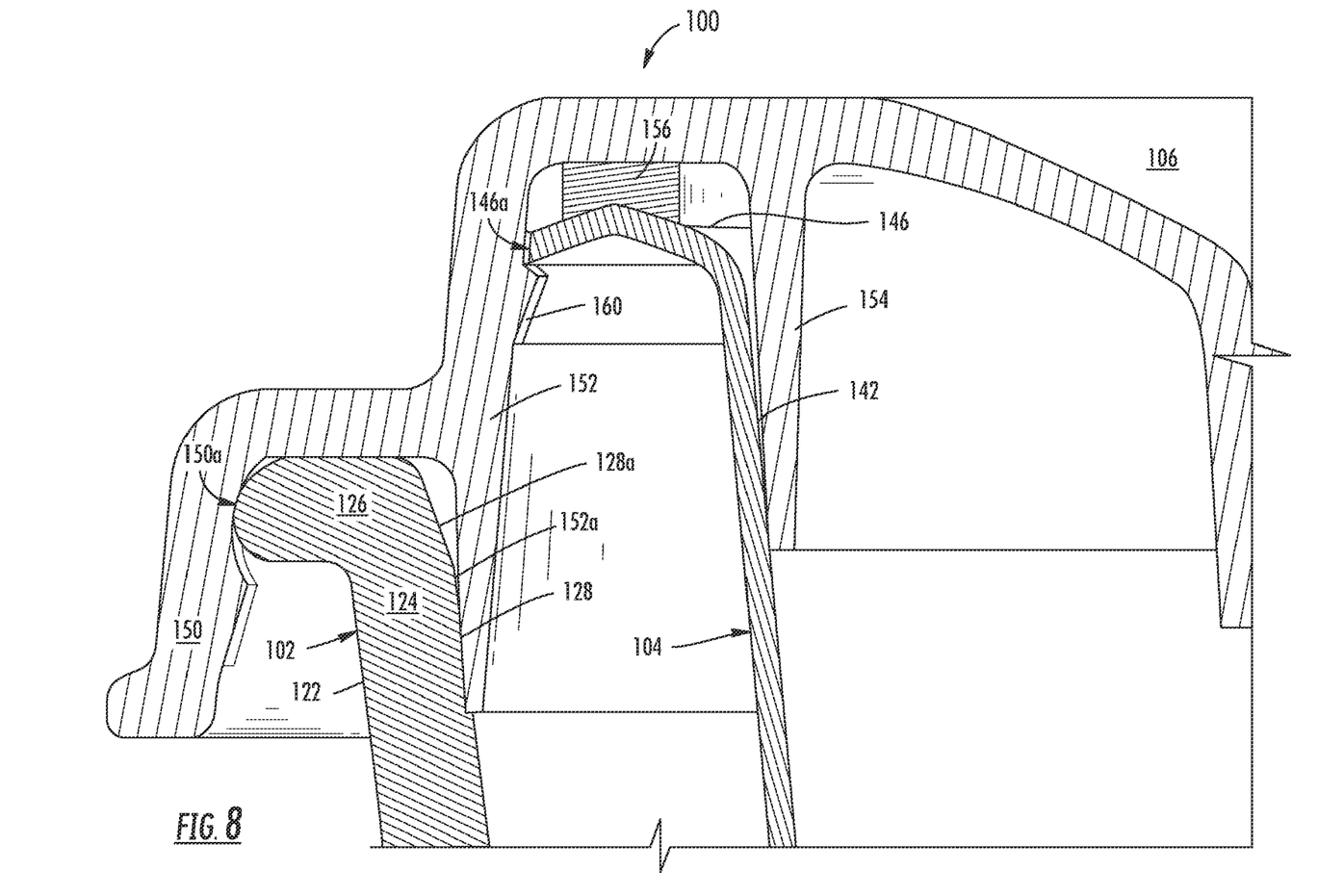
FIG. 8 shows an alternate embodiment of a suction system according to the disclosure.

With reference now to FIG. 8, there is shown an alternate embodiment of a medical suction system 100 having a rigid canister 102, a semi-rigid liner 104, and a lid 106. The system 100 is compatible with the mount 18 in the manner previously described and is substantially similar to the system 10, except for the differences herein noted.

The canister 102 is essentially cup-shaped with a bottom and a surrounding sidewall 122 extending from the bottom to an open upper end. The upper end of the canister 102 includes a single peripheral upstanding member 124 defined by an upper end of the sidewall 122. To facilitate a snap-fit relationship between the canister 102 and the lid 106, the upstanding member 124 includes a terminal end shaped to have a flange 126 configured to snap-fit with the lid 106. In addition, the upstanding member 124 also includes an inner chamfered edge 128 configured to engage a portion of the lid 106 to provide a seal between the exterior of the liner 104 and the atmosphere, described in more detail below. An upper portion 128a of the edge 128 is preferably oriented at a shallower pitch to provide a guide for facilitating seating of the lid 106.

The liner 104 is substantially identical to the liner 14, except that sidewall 142 of the liner 104 is taller than the sidewall 42 of the liner 14 so that it extends above the flange 126 by a distance of about 0.20 inches, and includes a flange 146 instead of the flange 46. The flange 146 extends outwardly from the upper open end of the liner 104 in the manner of the flange 46, except the flange 146 has a cross-sectional profile corresponding to an inverted V or chevron shape.

The lid 106 includes a peripheral snap ring 150 defining the outer periphery, a peripheral seal ring 152 extending from the interior surface of the lid 106, and a peripheral pilot ring 154 interior the seal ring 152. The ring 150 is stepped down from the portion off the lid adjacent the seal ring 152 a distance corresponding to the distance that the flange 146 of the liner 104 extends above the flange 126 of the canister 102. An adhesive material 156 is provided as a peripheral ring between the seal ring 152 and the pilot ring 154. The adhesive material 156 is preferably identical to the adhesive 56. The lid 106 also includes ports, such as the ports 58a-58d previously described.

An inner surface 150a of the snap ring 150 is shaped to matingly engage the shape of the flange 146. The inner seal ring 152 is tapered so as to provide an outer tapered surface 152a configured to fittingly engage the inner chamfered edge 128a and provide a seal along the interface of the edge 128a and the surface 152a, so as to seal between the atmosphere and the outside of the liner 104. A stop 160, such as a peripheral ledge or a plurality of projections or barbs, is located on the interior surface of the seal ring 152 and located so as to support a free edge 146a of the flange 146 when the lid 106 is installed. The pilot ring 154 is configured to extend just interior the sidewall 142 of the liner 104 and cooperates with the greater height of the sidewall 142 of the liner 104 so that the lid 106 is self-aligning with the liner 104 and the canister 102 in which the liner is installed.

The configuration of the system 100 is effective to inhibit the flange 146 of the liner 104 from pulling away from the adhesive 156, such as during extended periods of use. For example, the stop 160 cooperates with the chevron shape of the flange 146 for ease of a snap-fit installation, while providing a surface which engages the flange 146 in vacuum conditions during which the lid 106 is being urged away from the adhesive 156. That is, the stop 160 functions to deflect the chevron-shaped flange 146 upward, causing the effective diameter to increase, making it more difficult for the flange 146 to pass over the stop 160, and hence for the lid to separate from the adhesive 156.

The foregoing description of preferred embodiments for this disclosure has been presented for purposes of illustration and description. It is not intended to be exhaustive or to limit the disclosure to the precise form disclosed. Obvious modifications or variations are possible in light of the above teachings. The embodiments are chosen and described in an effort to provide the best illustrations of the principles of the disclosure and its practical application, and to thereby enable one of ordinary skill in the art to utilize the disclosure in various embodiments and with various modifications as are suited to the particular use contemplated. All such modifications and variations are within the scope of the disclosure as determined by the appended claims when interpreted in accordance with the breadth to which they are fairly, legally, and equitably entitled.

What is claimed is:

1. A suction system, comprising:
    a canister;
    a liner receivable within the canister and having an outwardly extending flange; and
    a lid positionable on the liner and the canister when the liner is received within the canister, the lid having a peripheral snap ring having one or more surfaces configured to engage portions of the canister in a snap-fit relationship, a peripheral seal member spaced interiorly apart from the snap ring and extending from an interior surface of the lid and positionable to engage and bear against an upstanding portion of the canister to provide a seal between the atmosphere and exterior portions of the liner located within the canister, and a peripheral adhesive material adhered to the interior surface of the lid adjacent the peripheral seal member and positionable to adhere to the flange of the liner when the lid is installed on the liner to provide a seal between the interior of the liner and locations exterior the liner.

2. The system of claim 1, wherein the liner includes a plurality of alignment tabs extending outwardly from the flange for aligning the lid with the liner.

3. The system of claim 1, wherein the canister has an open upper end that includes a first peripheral upstanding member adjacent the upper end and a second peripheral upstanding member adjacent the upper end and located radially outwardly of the first peripheral upstanding member and having a height greater than the height of the first peripheral upstanding member.

4. The system of claim 3, wherein the liner has an upper open end that includes an outwardly extending peripheral flange, the flange being supported by the first peripheral upstanding member of the canister when the lid is installed.

5. The system of claim 4, wherein the peripheral snap ring matingly engages the second peripheral upstanding member when the lid is installed.

6. The system of claim 1, wherein the lid further includes a pilot ring configured to extend interior a sidewall of the liner for aligning the lid with the liner.

7. The system of claim 1, further comprising a source of negative pressure, a first port extending through the lid for placing the interior of the liner in flow communication with the source of negative pressure, a second port extending through the lid for entry of fluids from a patient as a result of negative pressure being applied to the interior of the liner.

8. The system of claim 1, wherein the liner includes a chevron-shaped flange and an interior surface of the peripheral seal member of the lid includes a stop configured to engage the chevron-shaped flange to inhibit separation of the lid from the adhesive when the lid is installed.

9. The system of claim 1, wherein the adhesive comprises a pressure sensitive adhesive.

10. A suction system, comprising:
    a canister;
    a liner receivable within the canister and having an outwardly extending flange; and
    a lid positionable on the liner and the canister when the liner is received within the canister, the lid having a peripheral snap ring having one or more surfaces configured to engage portions of the canister in a snap-fit relationship, a peripheral seal member spaced interiorly apart from the snap ring and extending from an interior surface of the lid and positionable to bear against a portion of the canister to provide a seal between the atmosphere and exterior portions of the liner located within the canister, a pilot ring configured to extend interior a sidewall of the liner for aligning the lid with the liner, and a peripheral adhesive material adhered to the interior surface of the lid adjacent the peripheral seal member and positionable to adhere to the flange of the liner when the lid is installed on the liner to provide a seal between the interior of the liner and locations exterior the liner.

* * * * *